United States Patent
Chamoun et al.

(10) Patent No.: US 6,338,713 B1
(45) Date of Patent: *Jan. 15, 2002

(54) SYSTEM AND METHOD FOR FACILITATING CLINICAL DECISION MAKING

(75) Inventors: Nassib G. Chamoun, Needham; Philip H. Devlin, Brookline, both of MA (US)

(73) Assignee: Aspect Medical Systems, Inc., Newton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/135,931

(22) Filed: Aug. 18, 1998

(51) Int. Cl.[7] .................................................. A61N 5/00

(52) U.S. Cl. ....................................................... 600/300

(58) Field of Search ........................... 60/300, 475, 508, 60/509, 534

(56) References Cited

U.S. PATENT DOCUMENTS

| | | | |
|---|---|---|---|
| 4,517,986 A | * 5/1985 | Bilgutay | 128/671 |
| 5,195,531 A | 3/1993 | Bennett | |
| 5,458,117 A | 10/1995 | Chamoun et al. | |
| 5,590,650 A | * 1/1997 | Genova | 128/630 |
| 5,913,308 A | * 6/1999 | Forbes et al. | 128/700 |
| 5,924,980 A | * 7/1999 | Coetzee | 600/300 |

FOREIGN PATENT DOCUMENTS

WO     WO 97 15230     5/1997

OTHER PUBLICATIONS

Jyh–Shyan Lin et al: "Reduction of False Positives in Lung Nodule Detection Using a Two–Level Neural Classification", IEEE Inc., New York, vol. 15, No. 2, Apr. 1996, pp. 206–217.

Ueno, S. et al.: "Automatic Pattern Recognition of the Electroencephalogram under General Anesthesia during Surgical Operations", Memoirs of the Faculty of Engineering, Kyushu University, Dec. 1978, Japan, vol. 38, No. 4, pp. 419–430.

* cited by examiner

*Primary Examiner*—Max Hindenburg
(74) *Attorney, Agent, or Firm*—Hale and Dorr LLP (57) ABSTRACT

Disclosed is a system and method for providing information to the user of a medical monitoring or diagnostic device to aid in the clinical decision making process. The preferred embodiment uses two estimators or predictors of the same physiological quantity, with each of the estimators being designed to detect specific states or artifacts in the estimated parameter and thus operating at a different point on its respective ROC curve; one chosen to provide high sensitivity, the other chosen to provide high specificity. The divergence between the estimators is indicated by the use of a shaded region between their respective time trends. The use of 2 estimators of the same parameters with different performance characteristics allows the system and method of the present invention to derive additional information about the underlying physiologic process over and above that which would be available from a single estimator. The system and method of the present invention can derive information from not only the instantaneous values of the estimators and the difference between them, but also from the time trend of the difference.

28 Claims, 6 Drawing Sheets

SYSTEM AND METHOD FOR FACILITATING CLINICAL DECISION MAKING

BACKGROUND OF THE INVENTION

This invention relates to physiological monitoring systems and methods, and more particularly to physiological monitoring systems and methods which provide improved measurements of physiological parameters.

A medical monitoring or diagnostic device generally includes the ability to perform a measurement to obtain an estimate of the true value of a physiological parameter. This estimate is then used by a clinician to derive information concerning a patient's physical state, for the purpose of determining or monitoring a course of action with regard to the patient's medical care. An implicit assumption in this process is that the estimate of the physiological parameter provided by the measurement is identical to the actual, true value.

In actuality, the estimate of a parameter provided by a measurement has an inherent error, or difference between the estimated (measured) value and the true value. A measurement system may be such that it produces a random error (with an average value of zero), or it may be biased, such that the average error of the estimates is not equal to zero.

Concepts well understood in medical science are that of the sensitivity and specificity of a test. A binary estimate is one that can have 1 of 2 values: positive or negative, yes or no, present or absent, etc. For example, in the case of a binary parameter whose value can be positive or negative, the probability that any one measurement or estimate yields a positive response or prediction when the true value actually is positive is the "sensitivity" of the measurement. The sensitivity is thus the probability of detecting a true positive outcome. The probability that any one measurement or estimate yields a negative response or prediction when the true value actually is negative is the "specificity" of the measurement. The specificity is thus the probability of detecting a true negative outcome.

An ideal estimate or predictor would be one whose sensitivity and specificity are both 100%; that is, one in which there is zero probability of false detection, either false positive or false negative. Physically realizable measurements, however, rarely achieve this ideal. They instead typically have both sensitivity and specificity less than 100%.

Figure 1:
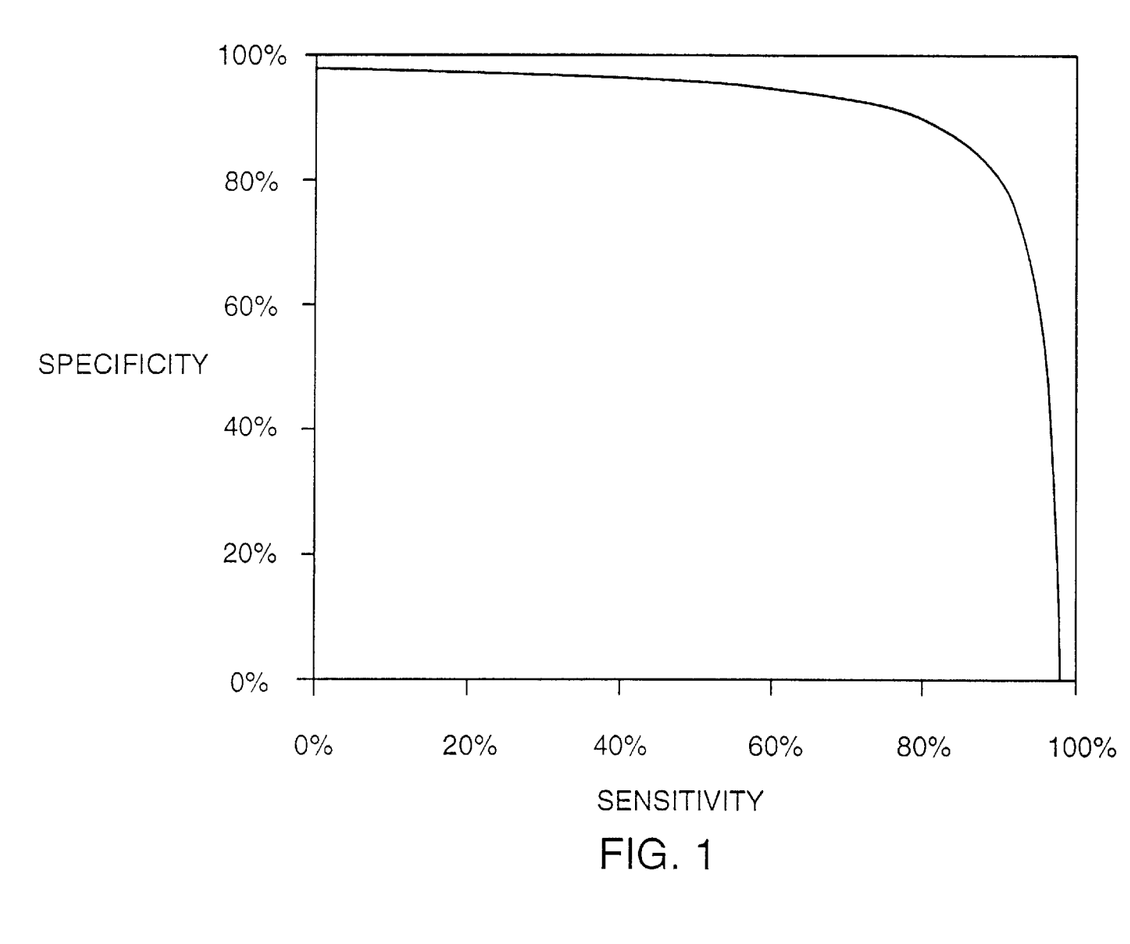
FIG. 1 is a graph of a hypothetical Receiver Operating Characteristic (ROC) curve.

It is well known in the art that the sensitivity and specificity of a measurement system can be biased by design either toward higher sensitivity at the expense of lower specificity, or toward higher specificity at the expense of lower sensitivity. The possible operating points of a measurement system can be described by the Receiver Operating Characteristic (ROC) curve. A hypothetical ROC curve is shown in FIG. 1. Actual ROC curves may be of different forms, but all exhibit a trade-off of sensitivity for specificity.

Figure 2:
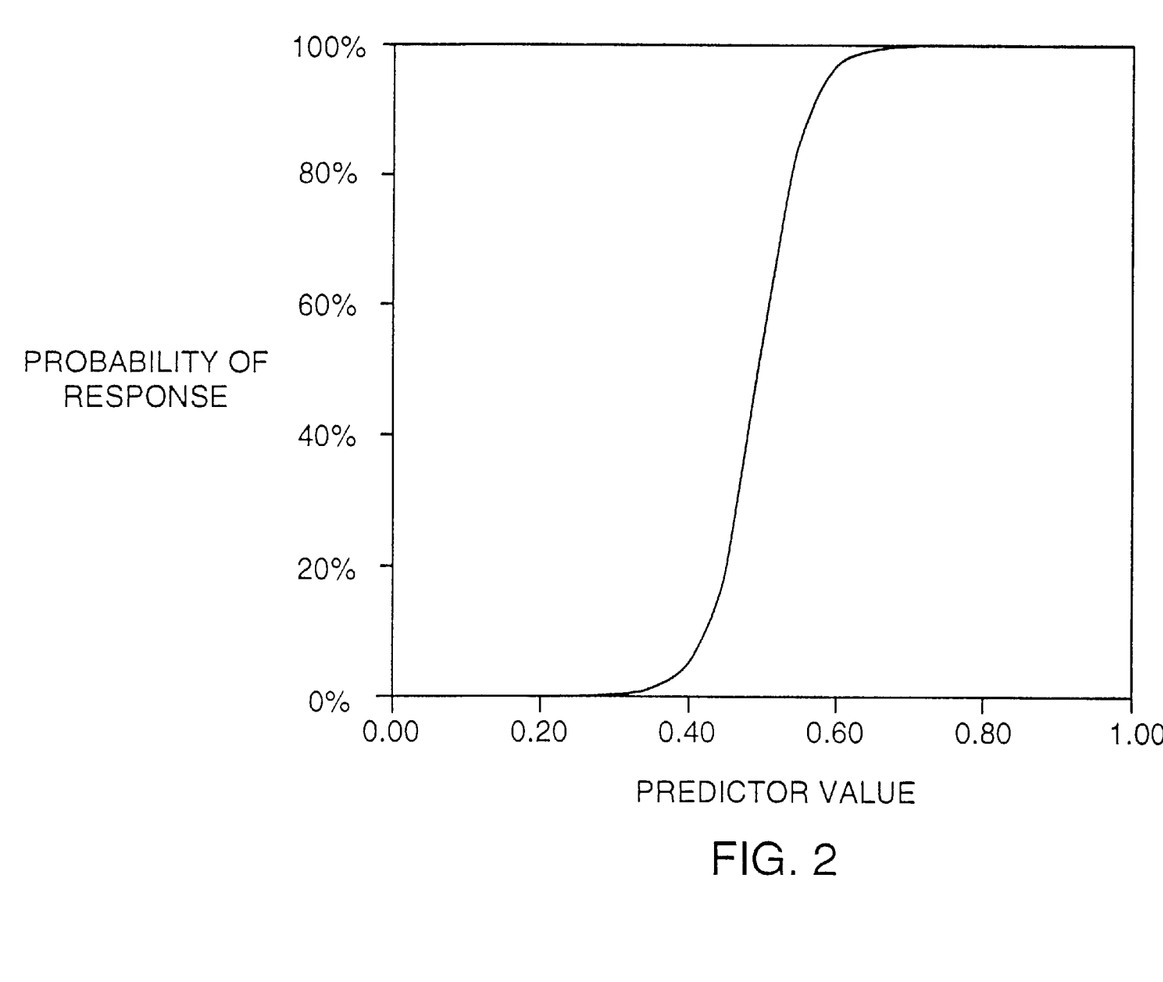
FIG. 2 is a graph of a hypothetical Probability of Response curve.

A binary estimate of a binary parameter translates directly to a predicted value for the parameter. It is also well understood in the art that predicted values can be obtained from continuous estimators. A threshold value may be applied to a continuous estimator of a binary parameter in order to provide a binary prediction. For example, if the value of the estimate is less than the threshold, the parameter is predicted to have one of the binary states. If the value of the estimate is greater than or equal to the threshold, the parameter is predicted to have the other binary state. The relationship between the estimator and the parameter may be modeled from experimental data as a probability of response, as shown in FIG. 2. The value of the estimator at which the probability of response is 50% is used as the threshold value in the preferred embodiment.

In a similar manner, multiple thresholds may be applied to a continuous estimator to predict the value of an ordinal parameter. For example, the Modified Observer's Assessment of Alertness/Sedation scale is commonly used to quantify an anesthetized surgical patient's level of sedation. A set of five ordinal thresholds may be applied to a single continuous estimator of the patient's sedation state to obtain a predicted sedation state.

| MODIFIED OBSERVER'S ASSESSMENT OF ALERTNESS/SEDATION SCALE | |
|---|---|
| RESPONSE | SCORE LEVEL |
| Responds readily to name spoken in normal tone | 5 |
| Lethargic response to name spoken in normal tone | 4 |
| Responds only after name is called loudly and/or repeatedly | 3 |
| Responds only after mild prodding or shaking | 2 |
| Does not respond to mild prodding or shaking | 1 |
| Does not respond to test stimulus | 0 |

The case of a continuous estimator used to predict an ordinal parameter may be extended to that of a continuous estimator used to predict the value of a continuous parameter. The relationship between the estimator and the parameter it predicts need not be linear, just as the threshold need not be evenly spaced in the case of an ordinal estimator. Any continuous parameter (e.g., a patient's state of sedation) may be considered to be a set of discrete ordinal states, each of which may be estimated by applying an appropriate set of threshold values to the continuous predictor. While each state is distinct, they are all steps on a continuum of states from one end of the state range to the other. Thus the concept of a ROC curve may be applied to the overall continuum of states as well as any pair of states and the performance of the estimator may be tuned to vary its sensitivity and specificity with respect to the full range of the parameter. It is important to note that an explicit threshold need not be applied to a continuous estimator in order to use the ROC concept; the probability of response is implied through the correlation between the estimator and the underlying parameter.

If a physically realizable system does not have both 100% sensitivity and specificity, then an important design issue is the point on the ROC curve corresponding to the actual sensitivity and specificity of the measurement. This is the operating point. In the case of a continuous estimator, varying the threshold value shifts the operating point along the ROC curve. The optimal location for the operating point on the ROC curve is preferably derived by means of a cost-benefit analysis. Weighing the cost of a false detection (both false positive and false negative) against the benefit of a correct detection performs such an analysis. When the cost and benefit are not equivalent, it may be desirable to shift the operating point to bias the prediction toward increased sensitivity or specificity. For example, a system designed to screen patients for the presence of a fatal disease may be designed to have very high sensitivity at the expense of low specificity. The increased detection rate afforded by the elevated sensitivity may be well worth the extra testing required to rule out false positives. The design procedure, however, requires that a choice be made between high sensitivity and high specificity in order to specify an operating point.

U.S. Pat. No. 4,517,986 issued to Bilgutay teaches the use of a series of amplifiers with different sensitivities in order to correctly measure blood pressure from pressure pulse waves of different amplitudes. This patent, however, teaches only the use of a set of amplifiers with different transfer functions to amplify different parts of the pressure waveform. It does not teach selecting different points on the ROC curve, or using the divergence between simultaneous estimators as a measure of deriving information about blood pressure.

It is therefore a principal object of the present invention to provide a system and method for measuring physiological parameters that provide more information concerning the measured physiological parameter than known systems.

Another object of the present invention is to provide a system and method for measuring physiological parameters that uses multiple simultaneous estimators.

SUMMARY OF THE INVENTION

The system and method of the present invention provides information to the user of a medical monitoring or diagnostic device to aid in determining the true state of the measured parameter. The preferred embodiment uses two or more estimators or predictors of the same physiological process. Each of the estimators is designed to detect or predict either a specific state of the underlying parameter, or alternatively a type or class of artifact. Each estimator will therefore have a different sensitivity and specificity with respect to predicting a specific state or artifact, and thus will have a different operating point on the ROC curve corresponding to the prediction of that state or artifact. The estimators are designed such that they have similar values in the absence of the states or artifacts they are designed to predict. Furthermore, they are designed so that the degree of divergence between the estimators in the presence of specific states or artifacts will be similar across a population. The use of two or more estimators of the same parameter with different performance characteristics allows the user of the system and method of the present invention to derive information from not only the values of the estimators but also from the degree of their divergences. This enables the user to derive additional knowledge about the underlying measured parameter or state over and above that which would be available from a single estimator. The system and method of the present invention can derive information from not only the instantaneous values of the estimators and their divergences, but also from the time trend of the values of the estimators and their divergences.

These and other objects and features of the present invention will be more fully understood from the following detailed description which should be read in light of the accompanying drawings.

DETAILED DESCRIPTION OF THE PREFERRED EMBODIMENT

It is well known in the state of the art that EEG data is predominantly contained in the frequency range of 0–40 Hz. Lighter states of anesthesia (i.e., those tending toward consciousness) are typically characterized by an increased amount of electrical power in the EEG frequency band of 20–40 Hz. Thus, an estimator intended to predict whether or not a patient was conscious might use the amount of power in this frequency band. An increased amount of power would predict an increased probability that the patient was conscious.

It is also well known that electromyographic (EMG) signals, the electrical activity arising from muscles, are predominantly contained in the frequency range of 30–300 Hz. EMG signals may thus appear in the same frequency range as EEG signals. EMG activity tends to increase as an anesthetized patient approaches consciousness. This EMG activity tends to increase power in the 30–40 Hz frequency band in conjunction with that of the EEG, enhancing the ability of the power in the 20–40 Hz band to predict consciousness. Increasing EMG activity, however, may also occur in a deeply anesthetized (deep) patient in conjunction with movement associated with reflexive motor activity. In this situation, the EMG activity tends to increase power in the 30–40 Hz frequency band, providing an effect on the estimator which is in opposition to that of the EEG. This increases the probability of a false prediction of consciousness and detracts from the overall performance of a diagnostic estimate of EEG activity based on the 20-40 Hz frequency band.

A preferred embodiment of this invention uses two (2) different estimators to predict the state of consciousness of a patient under anesthesia. Each of the estimators is designed to have a value that is reflective of the probability that the patient is conscious. In addition, one of the estimators is designed to detect the presence of EMG activity. The estimators will have nearly identical values in the absence of EMG activity, and will diverge in the presence of EMG activity. The estimators thus have different sensitivity and specificity with respect to the prediction of consciousness and the presence of EMG activity. The instantaneous value of each of the estimators is trended over time, and a shaded region is created on the trend display to graphically indicate the divergence between the two (2) estimators. The width of the shaded region is thus indicative of the degree to which EMG activity is influencing the estimation of the patient's state of consciousness, thereby imparting additional clinical information about the underlying state of consciousness over and above that of each of the estimators alone. It should be noted that this embodiment may be easily extended to N estimators, where N is a number greater than two. Each of these additional estimators would be designed to detect some specific consciousness or EEG state or type of artifact, and to be similar to the others in the absence of the state or artifact it is designed to detect.

Figure 3:
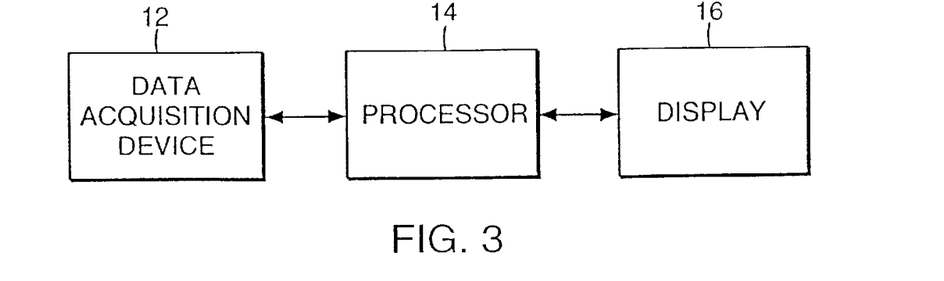
FIG. 3 is a block diagram of the functional components of a system of the present invention.

Referring to FIG. 3, a system for generating multiple estimators and representations of relationships with such estimators is shown. Data acquisition device 12 can be any device suitable for obtaining physiological signals from a human body and converting them to a form for processing. Processor 14 processes such signals and computes the estimators as described below. In addition, processor 14 will calculate the relationships between such estimators. Display 16, which in a preferred embodiment is a CRT display, can be any video, hard copy or other similar display used to display computer generated information. In certain embodiments where the representations of the estimators and the relationship between such estimators is graphical in nature, the output device should be able to display graphical images.

The actual form of the estimators is derived using an empirical design process. A development database is first created which contains segments of data that serve as prototypes of the states or artifacts to be identified. The database must contain recordings from a large number of test subjects so that it is representative of a broad population. In the preferred embodiment described above, the development database contains segments of EEG signals recorded at various awake and anesthetized states and during intraoperative muscle reflex movements in a wide variety of subjects. Estimators may be developed using various techniques that are common in the art, such as cluster or discriminant analysis. The estimators are designed such that they have similar values in the absence of the specific state or artifact they are designed to detect, and such that they have an approximately constant divergence across the entire population in the presence of the state or artifact they are designed to detect. It is important to recognize that other estimators may provide equivalent or even enhanced performance over those described in this preferred embodiment. The present invention does not depend on the form of the estimators.

Figure 4:
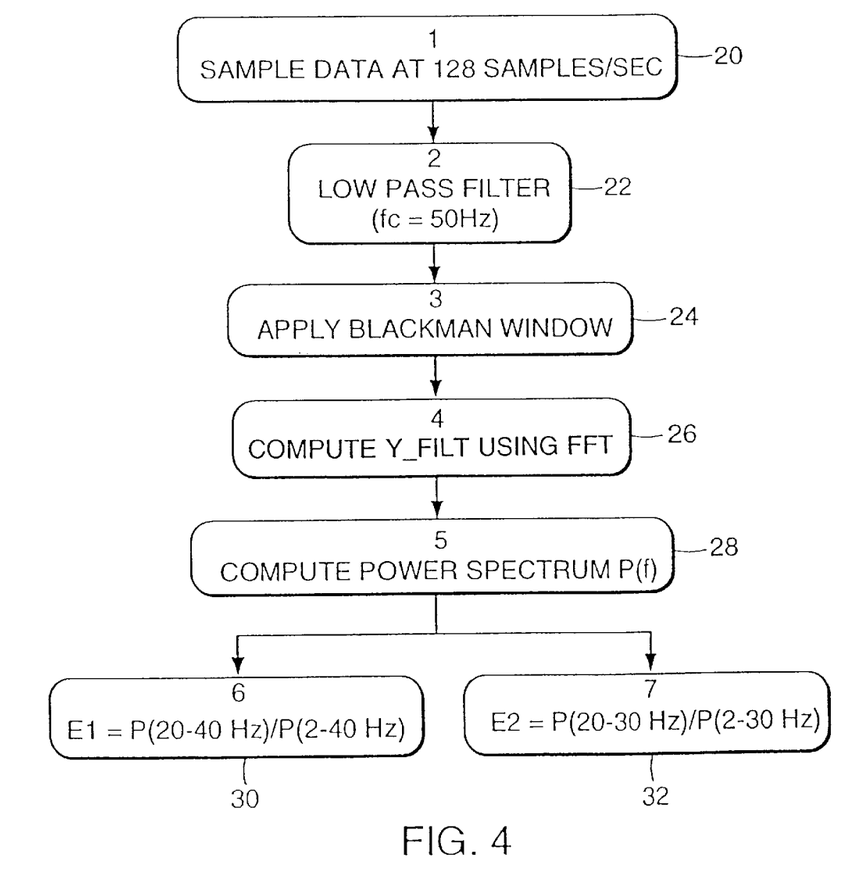
FIG. 4 is a block diagram of the process for the determination of the first and second estimators utilized in the preferred embodiment of the system and method of the present invention.

FIG. 4 is a block diagram of the process for calculating the estimators in the first preferred embodiment. In step 20, the EEG signal is first sampled at 128 Hz and separated into two second epochs $x_i$ for processing.

$x_i$ where i=1,2, . . . N

The variable N is the number of samples in the epoch; in this case, N=256. The data is low pass filtered in step 22 using a fifth order Butterworth filter with a corner frequency ($f_c$) at 50 Hz. This corner frequency was chosen to allow the entire EEG signal to pass through the filter, while excluding AC power line interference (60 Hz).

$y_i = b_i + b_2 x_{i-1} + b_3 x_{i-2} + b_4 x_{i-3} + b_5 x_{i-4} + b_6 x_{i-5} - a_2 Y_{i-1} - a_3 y_{i-2} - a_4 y_{i-3} - a_5 y_{i-4} - a_6 y_{i-5}$ where $b_1 = 0.3198$, $b_2 = 1.5990$, $b_3 = 3.1980$, $b_4 = 3.1980$, $b_5 = 1.5990$, $b_6 = 0.3198$ $a_2 = 2.7872$, $a_3 = 3.4091$, $a_4 = 2.1972$, $a_5 = 0.7377$, $a_6 = 0.1023$ In step 24, the filtered epoch $y_1$ is then multiplied by a Blackman window (w_blk) (J.N. Little, L. Shure, Matlab Signal Processing Toolbox User's Guide, The MathWorks, Inc. Natick, MA 1992, pg. 2–9) to improve spectral estimation, $$w\_blk_i = 0.42 - 0.5\cos\left(2\tilde{a}\frac{i-1}{N-1}\right) + 0.08\cos\left(4\tilde{a}\frac{i-1}{N-1}\right)$$

where i=1,2,3, . . . N $y\_filt_i = y_i w\_blk_i$

The filtered, windowed data is transformed into the frequency domain in step 26 by use of the Fast Fourier Transform (FFT) technique $$Y\_FILT_k = \sum_{i=0}^{N-1} y\_filt_i e^{\frac{-j2\tilde{a}ki}{N}}$$

where $$j = \sqrt{-1}$$

In the preferred embodiment, n=256 and thus $Y\_FILT_k$ contains 129 complex values, corresponding to frequencies ranging from 0 to 64.0 Hz in 0.5 Hz increments.

The power spectrum is computed as the squared magnitude of $Y\_FILT_k$ in step 28:

$$P_k = |Y\_FILT_k|^2$$

Pk contains 129 values, corresponding to power values at frequencies ranging from 0 to 64.0 Hz in 0.5 Hz increments.

The primary and secondary estimators are then calculated as $$E_1 = 100 \frac{\sum_{k=40}^{80} P_k}{\sum_{k=4}^{80} P_k}$$

$$E_2 = 100 \frac{\sum_{k=40}^{60} P_k}{\sum_{k=4}^{60} P_k}$$

Figure 5:
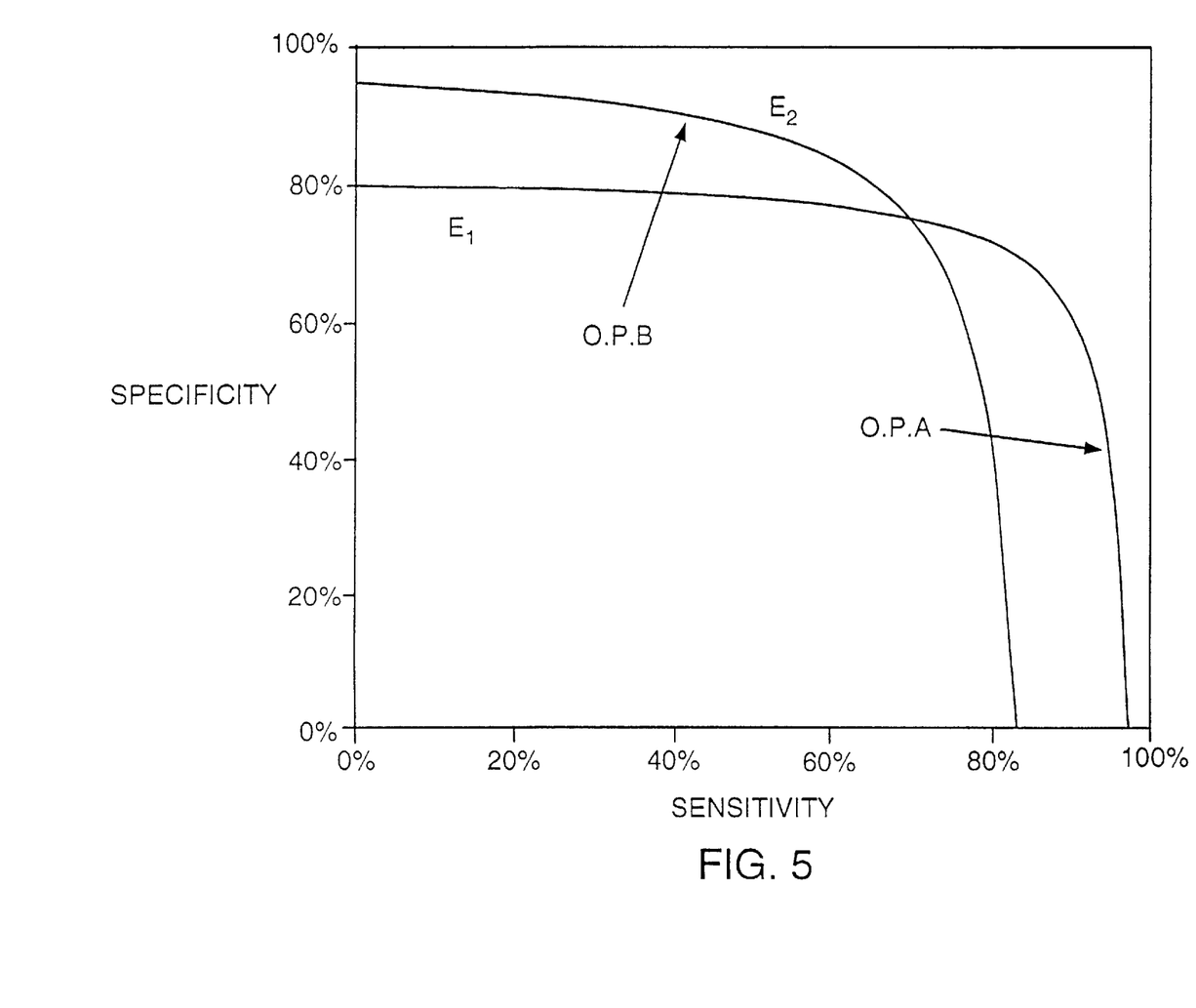
FIG. 5 is a graph of the ROC curves generated by the system and method of the present invention, in which each estimator (predictor) has a different ROC curve.

In steps 30 and 32, the estimators are calculated as a power in a specified frequency band relative to the power of the entire spectrum of interest, in percent. The estimator $E_1$ is the percentage of the total power (2–40 Hz) that is contained in the 20 to 40 Hz frequency band. Estimator $E_2$ is the percentage of the total power (2–30 Hz) that is contained in the 20 to 30 Hz frequency band. Estimator $E_1$ will be sensitive to the presence of EMG activity while estimator $E_2$ will not. In the absence of significant EMG activity, both estimators will have similar values since the 30 to 40 Hz frequency band will contain a negligible proportion of the total power. In this case, both will be reflective of the probability of consciousness as indicted by the power in the 20 to 30 Hz frequency band; higher power indicating an increased probability of consciousness, lower power indicating a lower probability of consciousness. In the presence of significant EMG activity, however, the value of $E_1$ will increase much more than that of $E_2$ and the values of the two estimators will diverge. Since increased EMG activity may be reflective of both increasing levels of consciousness as well as reflex movements in a deeply anesthetized (deeply unconscious) patient, $E_1$ will exhibit a higher sensitivity to an increased level of consciousness than $E_2$. Conversely, $E_2$ will exhibit a higher specificity to an increased level of consciousness than $E_1$. The effect of the design process is to produce two (or more) estimators of the same parameter that may have different ROC curves and different operating points (OP) on their respective curves. As shown in FIG. 5, estimator El operating at OP A provides predicts consciousness with a high sensitivity, while estimator $E_2$ operating at OP B provides high specificity.

The divergence between the values of the estimators serves as an indicator of confidence in the prediction. When the estimators are in agreement (i.e., little or no divergence), the user can be confident that the specific states or artifacts that would be indicated by the divergence are not present and that the underlying parameter is being estimated with a high degree of accuracy. A divergence between the estimators indicates to the user the need for careful assessment of the situation. In a preferred embodiment, a divergence indicates the need for the user to utilize clinical judgement and clinical endpoints to determine which estimator more accurately reflects the state of the patient. If, for example, in the middle of surgery, $E_1$ suddenly increases while $E_2$ does not, an anesthesiologist must consider the level of sedative and analgesic agents administered to the patient. If these indicate that the patient should be deeply anesthetized and there is no concomitant increase in heart rate or blood pressure, then estimator $E_1$ has probably increased in response to a reflex movement. Since reflex movements are unrelated to the patient's anesthetic brain state, estimator $E_2$ will more accurately reflect the probability of consciousness. In contrast, if both estimators are increasing over time at the end of a case in response to a decreased dose or cessation of the administration of anesthetic agent and $E_1$ suddenly increases rapidly, the likely cause is increasing muscle tone due to returning consciousness. In this case, $E_1$ will be the more reliable predictor of the probability of consciousness. In all cases when the estimators diverge, it is a prompt to the clinician to consider "How did we get here?".

Figure 6:
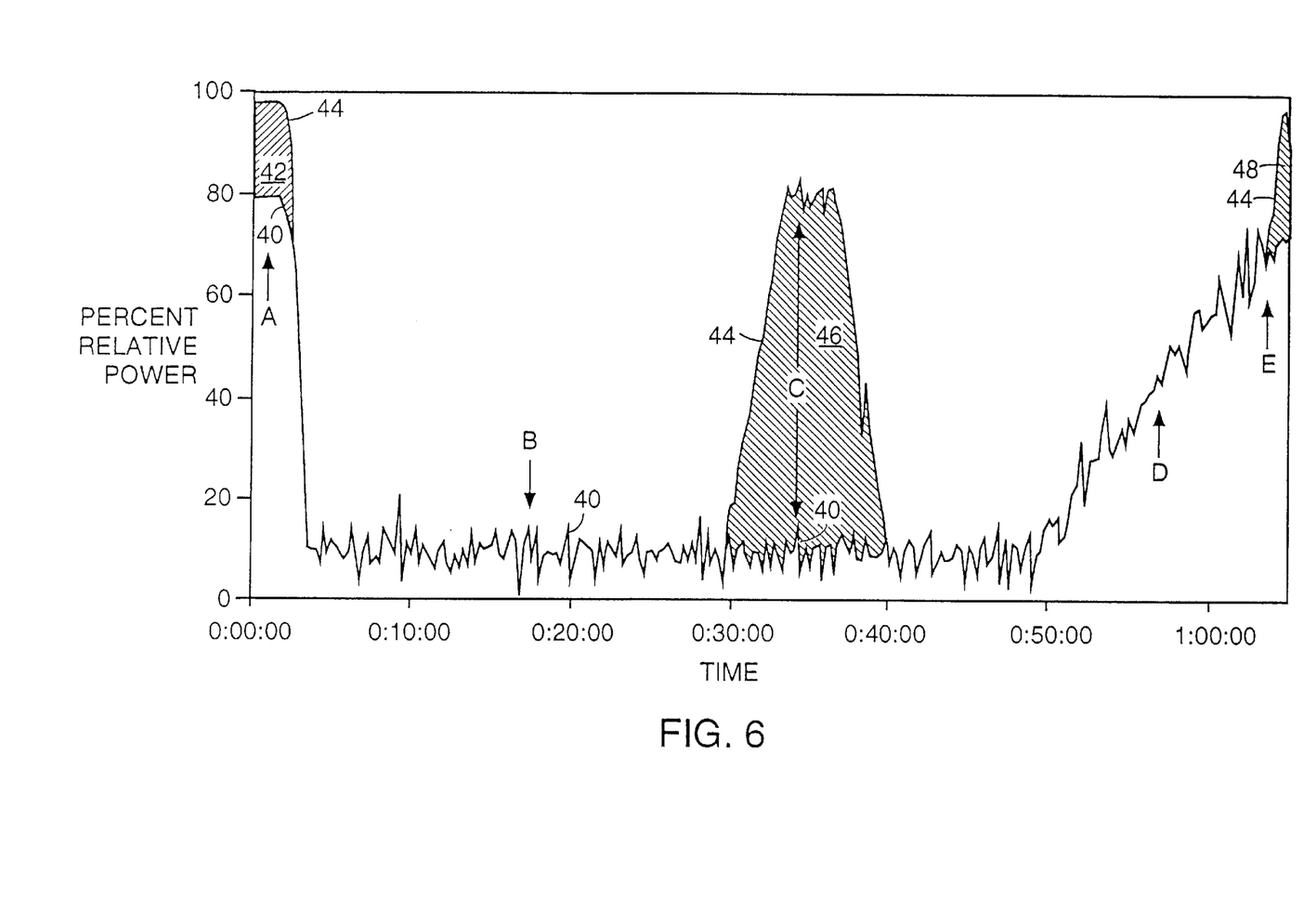
FIG. 6 is a graph of the time trend of the two estimators (predictors) generated by the system and method of the present invention in which the shaded region indicates the divergence between the two estimators.

FIG. 6 shows a sample trend of the two estimators and their divergence during a typical surgical case. At point A, the beginning of the surgical case, the patient is conscious. Both estimators are at high values, indicating a light anesthetic state and a high probability of consciousness. The high value of $E_2$ (heavy line) 40 indicates a substantial contribution to the 20–40 Hz power from the EEG. The shaded divergence region 42 indicates that EMG activity contributes even more power, confirming the prediction of consciousness. At point B the two estimators are identical, both predicting a deep anesthetic state. The absence of a shaded divergence region indicates a high degree of confidence in the prediction of a low probability of consciousness.

At point C, estimator $E_1$ (thin line) 44 is indicating a light anesthetic state, while estimator $E_2$ (heavy line) 40 is indicating a deep anesthetic state. The wide divergence indicated by the shaded region 46 indicates a need to interpret this data in light of clinical judgement and other clinical endpoints. The sudden increase in $E_1$ occurred intraoperatively at a time when the patient had been administered doses of anesthetics generally considered adequate, and there was no sudden increase in surgical stimulation. For this reason, the increase in $E_1$ is most likely due to a burst of EMG activity arising from an involuntary reflex movement, indicating that $E_2$ is the more accurate assessment of the patient's state of consciousness.

At point D, both estimators are trending upward, indicating a change in the patient to a lighter state of anesthesia. The absence of a divergence between the two estimators indicates that all the power in the 20–40 Hz region is coming from the EEG, and indicates a high level of confidence in the prediction.

At point E, the wide shaded divergence region 48 cautions the anesthesia provider to use clinical judgement to determine which estimator is more representative of the actual patient state. Both estimators have been trending up indicating an EEG state tending toward increased probability of consciousness. Since this occurs at the end of the case, the divergence is most likely due to increased basal EMG activity associated with returning consciousness and indicates that predictor $E_1$ more accurately reflects the state of the patient.

In this example, the differing sensitivity and specificity characteristics of the two estimators (predictors) which result from their differing operating points on their respective ROC curves are clearly demonstrated. The shaded divergence region directs the attention of the anesthetic provider to divergences between the patient state predicted by the different estimators and thus serves as an indicator of the level of confidence to be placed in the joint prediction and whether the provider needs to exercise extra clinical judgment in the interpretation.

Figure 7:
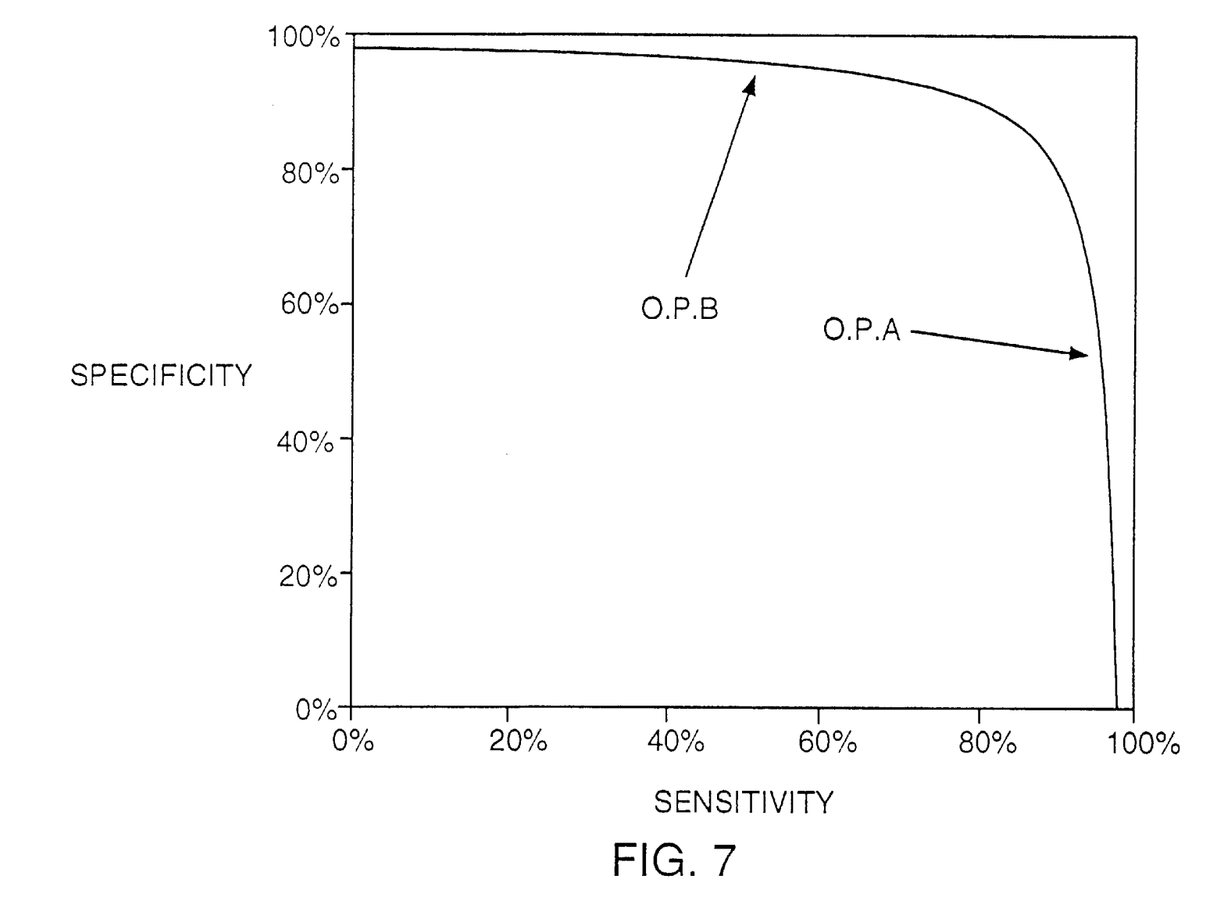
FIG. 7 is a graph of the ROC curves generated by an alternate embodiment of the system and method of the present invention, in which each estimator (predictor) has an identical ROC curve.

The preceding embodiment utilizes two estimators (predictors) with different ROC curves to estimate the same parameter. An alternate embodiment utilizes two estimators (predictors) with identical ROC curves. The ROC curve for such an embodiment is shown in FIG. 7. The operating points may be chosen so that one operating point (O.P. A) provides a high sensitivity at the expense of lower specificity, while the second operating point (O.P. B) provides high specificity at the expense of lower sensitivity. It should be noted that such an alternate embodiment, utilizing two estimators (predictors) with identical ROC curves, is functionally equivalent to the use of two different operating points on the ROC curve of a single estimator (predictor). Such a system could be implemented using a single estimator by using two different values of the estimator as thresholds defining a positive or negative prediction, corresponding to the different operating points.

While the preferred embodiment described above incorporates 2 estimators, the invention is easily extended to an alternate embodiment of N estimators, where N is a number greater than 2. In this case, additional estimators are incorporated which are designed to predict specific EEG or consciousness states or specific types or classes or signal artifact. For example, one estimator might be designed to detect the presence of low frequency EEG activity reflective of deep anesthetic states with a low probability of consciousness. A second might be designed to detect the presence of high frequency EEG reflective of lighter anesthetic states. A third might be designed to detect the presence of high frequency noise resulting from external electromagnetic interference. And a fourth might be designed to detect the presence of eye movement artifact. Each of these predictors would be designed to have similar values in the absence of the states or signals they are designed to detect. They would also be designed to have roughly constant divergences in response to similar signal situations across a broad population of subjects. Divergences may be indicated between each pair of estimators, or between selected estimators only.

Additionally, it should be recognized that many methods in addition to power spectral analysis may be used to compute estimators. These include, but are not limited to, bispectral and higher order spectral analysis, time domain analysis methods, and stochastic and non-parametric modeling. This invention is not intended to be limited to any of the analysis methods described in the preferred or alternate embodiments.

The utility of estimating and displaying a range of predicted probabilities for a specific endpoint (e.g., consciousness) bounded by two different operating points is useful in the field of cardiology as well. For example, early detection of significant coronary artery disease (CAD) in a patient is useful in minimizing the risk of a heart attack (i.e., early diagnosis enables early therapy or change in lifestyle that may inhibit the progression of heart disease). A cardiac index which predicts the presence of significant CAD can be constructed from parameters or features derived from the QRS complex, the primary triangular component of the surface ECG waveform. For example, a set of features which may predict the presence of CAD include QRS duration, average QRS bicoherence (600<f1+f2<1000 Hz) and QRS power. Using a database of ECGs from healthy and diseased patients, a logistic model of a linear combination of these same features can be constructed which predicts the presence of significant CAD. An alternate embodiment of this invention, therefore, utilizes two models using these features, one model tuned for high sensitivity, the other tuned for high specificity. Subsequently, new patients can be evaluated for the presence of significant CAD by evaluating both predictive models. The result would be a lower and upper bound on the probability of CAD for the patient. In many instances, the range would be tight (e.g., for older men, or young women). In other cases, the range would be wide (e.g., for middle-aged women). The level of uncertainty would be reflected in the range of predicted probabilities. The estimation of the probability of CAD using each of the two models would produce a single value for each estimator, so these estimators (probabilities) would not be trended in time. However, the level of uncertainty indicated by the divergence between the estimators may be represented graphically by shading the region between them on a display device.

The notion of providing a range of predicted probabilities may be extended from using one estimator evaluated at two different operating points to using two different estimators (using different features, for example) in which one predictor would be highly sensitive while the other predictor would be highly specific. For example, in the application of a set of predictors of consciousness, an accurate eye blink detector derived from the electrooculogram (EOG) would be a very specific detector for consciousness, but would be fairly insensitive. That is, the presence of eye blinks indicates consciousness; however, people can be conscious without creating eye blinks. In contrast, the previously mentioned EEG derived estimator $E_1$ is highly sensitive to conscious states, but is less specific. Separate estimates of the probability of consciousness derived from the EEG and EOG would provide a upper and lower bounds of the probability of consciousness in a manner similar to the two EEG derived predictors described earlier.

While the foregoing invention has been described with reference to its preferred embodiments, various alterations and modifications will occur to those skilled in the art. All such alterations and modifications are intended to fall within the scope of the appended claims.

What is claimed is:

1. A system for evaluating values of physiological parameters, said system comprising:
   a signal acquisition device for obtaining physiological signals from a human body;
   a processor for deriving, from said physiological signals, values of two or more independently-calculated estimators of a pre-selected physiological parameter and for computing relationships between said estimators;
   a display for displaying information concerning said relationships between said independently-calculated estimators.

2. The system for evaluating values of physiological parameters of claim 1, wherein one estimator is derived using one physical or computational method and wherein at least one other estimator is derived using a different physical or computational method.

3. The system for evaluating values of physiological parameters of claim 1, wherein said relationships computed by said processor are instantaneous differences between the values of each estimator.

4. The system for evaluating values of physiological parameters of claim 1, in which said processor uses an instantaneous value of a relationship between estimators to determine the width of an identifiable region about, below, or above an instantaneous value of the first estimator displayed by said display.

5. The system for evaluating values of physiological parameters of claim 1, in which said processor uses an instantaneous value of a relationship between estimators to determine graphical attributes of instantaneous values of a first estimator displayed by said display.

6. The system for evaluating values of physiological parameters of claim 1, in which said processor uses a measure independent of a first estimator of a parameter of interest to determine the width of an identifiable region about, below or above a first estimator displayed by said display.

7. The system for evaluating values of physiological parameters of claim 1, in which said processor uses a measure independent of a first estimator of a parameter of interest to determine graphical attributes of instantaneous values of a first estimator displayed by said display.

8. A system for evaluating values of physiological parameters, said system comprising:
   a signal acquisition device for obtaining physiological signals from a human body;
   a processor for deriving from said physiological signals, values of two or more independently-calculated estimators of a pre-selected physiological parameter;
   a display for displaying said independently-calculated estimators.

9. The system for evaluating values of physiological parameters of claim 8, wherein one estimator is derived using one physical or computational method and wherein at least one other estimator is derived using a different physical or computational method.

10. The system for evaluating values of physiological parameters of claim 8, wherein said processor also computes relationships between said estimators and wherein said relationships are instantaneous differences between the values of each estimator.

11. The system for evaluating values of physiological parameters of claim 8, in which said processor uses an instantaneous value of a relationship between estimators to determine the width of an identifiable region about, below, or above an instantaneous value of the first estimator displayed by said display.

12. The system for evaluating values of physiological parameters of claim 8, in which said processor uses an instantaneous value of a relationship between estimators to determine graphical attributes of instantaneous values of a first estimator displayed by said display.

13. The system for evaluating values of physiological parameters of claim 8, in which said processor uses a measure independent of a first estimator of a parameter of interest to determine the width of an identifiable region about, below or above a first estimator displayed by said display.

14. The system for evaluating values of physiological parameters of claim 8, in which said processor uses a measure independent of a first estimator of a parameter of interest to determine graphical attributes of instantaneous values of a first estimator displayed by said display.

15. A method for evaluating values of physiological parameters, said method comprising the steps of:

obtaining physiological signals from a human body;

deriving, from said physiological signals, values of two or more independently-calculated estimators of a pre-selected physiological parameter and computing relationships between said estimators;

displaying information concerning said relationships between said independently-calculated estimators.

16. The method for evaluating values of physiological parameters of claim 15, wherein one estimator is derived using one physical or computational method and wherein at least one other estimator is derived using a different physical or computational method.

17. The method for evaluating values of physiological parameters of claim 15, wherein said relationships are instantaneous differences between different estimators and instantaneous values of each estimator.

18. The method for evaluating values of physiological parameters of claim 15, in which an instantaneous value of a relationship between estimators is used to determine the width of an identifiable region about, below, or above an instantaneous value of the first estimator displayed by said display.

19. The method for evaluating values of physiological parameters of claim 15, in which an instantaneous value of a second estimator or a relationship between estimators is used to determine graphical attributes of an instantaneous values of a first estimator displayed by said display.

20. The method for evaluating values of physiological parameters of claim 15, in which a measure independent of a first estimator of a parameter of interest is used to determine the width of an identifiable region about, below or above a first estimator displayed by said display.

21. The method for evaluating values of physiological parameters of claim 15, in which a measure independent of a first estimator of a parameter of interest is used to determine graphical attributes of instantaneous values of a first estimator displayed by said display.

22. A method for evaluating values of physiological parameters, said method comprising the steps of:

obtaining physiological signals from a human body;

deriving, from said physiological signals, values of two or more independently-calculated estimators of a pre-selected physiological parameter;

displaying said independently-calculated estimators.

23. The method for evaluating values of physiological parameters of claim 22, wherein one estimator is derived using one physical or computational method and wherein at least one other estimator is derived using a different physical or computational method.

24. The method for evaluating values of physiological parameters of claim 22, further comprising the steps of computing relationships between said estimators and wherein said relationships are instantaneous differences between different estimators and instantaneous values of each estimator.

25. The method for evaluating values of physiological parameters of claim 22, in which an instantaneous value of a relationship between estimators is used to determine the width of an identifiable region about, below, or above an instantaneous value of the first estimator displayed by said display.

26. The method for evaluating values of physiological parameters of claim 22, in which an instantaneous value of a relationship between estimators is used to determine graphical attributes of an instantaneous values of a first estimator displayed by said display.

27. The method for evaluating values of physiological parameters of claim 22, in which a measure independent of a first estimator of a parameter of interest is used to determine the width of an identifiable region about, below or above a first estimator displayed by said display.

28. The method for evaluating values of physiological parameters of claim 22, in which a measure independent of a first estimator of a parameter of interest is used to determine graphical attributes of instantaneous values of a first estimator displayed by said display.

* * * * *